(12) United States Patent
McCord et al.

(10) Patent No.: US 8,614,427 B1
(45) Date of Patent: Dec. 24, 2013

(54) SUSPENDED MEMBRANE CALIBRATION SAMPLE

(75) Inventors: Mark A. McCord, Mountain View, CA (US); Liqun Han, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 1569 days.

(21) Appl. No.: 10/195,638

(22) Filed: Jul. 15, 2002

(51) Int. Cl.
*G01N 23/00* (2006.01)

(52) U.S. Cl.
USPC ............... 250/491.1; 250/492.2; 250/492.22

(58) Field of Classification Search
USPC .................................. 250/492.1, 310, 491.1
See application file for complete search history.

(56) References Cited

U.S. PATENT DOCUMENTS

| | | | |
|---|---|---|---|
| 6,320,187 B1 * | 11/2001 | Enichen | 250/252.1 |
| 6,384,408 B1 | 5/2002 | Yee et al. | |
| 6,403,971 B1 * | 6/2002 | Kawata | 250/491.1 |
| 6,521,392 B2 | 2/2003 | Yahiro | 430/296 |
| 6,538,753 B2 * | 3/2003 | Grodnensky et al. | 356/625 |
| 6,570,157 B1 * | 5/2003 | Singh et al. | 250/311 |
| 6,831,282 B2 * | 12/2004 | Yahiro | 250/492.22 |
| 6,842,230 B2 * | 1/2005 | Takakuwa et al. | 355/77 |
| 2003/0077530 A1 * | 4/2003 | Fujiwara et al. | 430/30 |
| 2003/0215965 A1 * | 11/2003 | Grodnensky et al. | 438/16 |

* cited by examiner

*Primary Examiner* — Phillip A Johnston
(74) *Attorney, Agent, or Firm* — Okamoto & Benedicto LLP

(57) ABSTRACT

One embodiment disclosed relates to a method for fabricating a calibration sample. The method includes lithographically patterning a first side of a wafer with a pattern of a self-supporting membrane, etching the first side of the wafer to form the self-supporting membrane in a layer on the first side, and etching a second side of the wafer to reach the layer so as to suspend the membrane over an empty space. Another embodiment disclosed relates to a charged particle beam system. The system includes a charged particle source, a focusing column and lens assembly, a detector, and a suspended membrane calibration sample. Another embodiment disclosed relates a suspended membrane calibration sample for a charged particle beam system. The calibration sample includes a plurality of calibration patterns in an array, a suspended membrane that is self-supporting and includes the plurality of calibration patterns, and an empty space underneath the membrane.

15 Claims, 16 Drawing Sheets

SUSPENDED MEMBRANE CALIBRATION SAMPLE

BACKGROUND OF THE INVENTION

1. Field of the Invention

The present invention relates generally to charged particle beam systems. More particularly, the present invention relates to an improved calibration sample for use in charged particle beam systems, such as electron beam systems and ion beam systems.

2. Description of the Background Art

Previous techniques for calibrating electron beam systems typically use silicon chips either with a patterned layer of material (typically oxide or gold), or deposited with specimens having naturally occurring patterns (such as fine metal grains). Disadvantageously, as a result of repeated exposure to electron beams, organic contamination frequently builds up on the surface of the silicon chip. Such a contamination layer may degrade the quality of the calibration image over time, resulting in variations in the calibration results and/or the need for periodic replacement of the calibration sample. Another disadvantage is that the contrast of these calibration samples is a function of the energy of the electron beam. As a result, systems that need calibration at multiple beam energies may have difficulty being calibrated due to the changing (or even inverting) contrast at different energies.

Gold grid calibration samples have also been used. Such grids may be made by punching a fine array of holes in gold foil. However, gold grids lack the fine features and sharp edges necessary to perform certain types of calibrations.

SUMMARY

One embodiment of the invention relates to a method for fabricating a calibration sample. The method includes lithographically patterning a first side of a wafer with a pattern of a self-supporting membrane, etching the first side of the wafer to form the self-supporting membrane in a layer on the first side, and etching a second side of the wafer to reach the layer so as to suspend the membrane over an empty space.

Another embodiment of the invention relates to a charged particle beam system. The system includes a charged particle source, a focusing column and lens assembly, a detector, and a suspended membrane calibration sample.

Another embodiment of the invention relates a suspended membrane calibration sample for a charged particle beam system. The calibration sample includes a plurality of calibration patterns in an array, a suspended membrane that is self-supporting and includes the plurality of calibration patterns, and an empty space underneath the membrane.

DETAILED DESCRIPTION

Embodiments of the present invention provide for a calibration sample for a charged particle beam system, such as an electron beam system or an ion beam system. The calibration sample advantageously may give calibration images that are of high contrast, relatively independent of landing energy and beam current, and relatively free of contamination. The calibration sample may be used for a variety of calibrations including deflection (field of view) calibration, focusing, astigmatism correction, stage calibration, beam size measurements, dynamic correction, beam alignment, image distortion and uniformity, and signal/noise measurements.

FIGS. 1A through 1G are cross-sectional diagrams illustrating various steps of a method for fabricating a calibration sample in accordance with one embodiment of the invention.

Figure 1A:
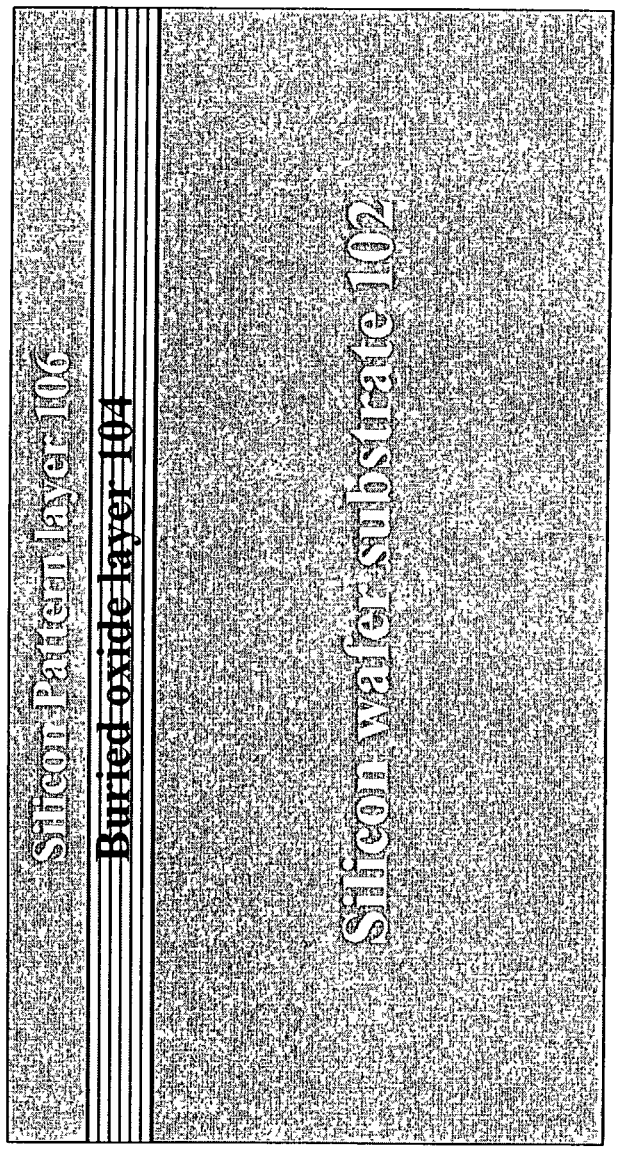
FIGS. 1A through 1G are cross-sectional diagrams illustrating various steps of a method for fabricating a calibration sample in accordance with one embodiment of the invention.

FIG. 1A is a cross section showing three layers of a starting wafer. In this instance, the three layers include a silicon wafer substrate 102, a buried oxide layer 104, and a silicon pattern layer 106. For example, the silicon substrate 102 may be about 500 micrometers (μm) thick, the buried oxide layer 104 may be about 0.5 μm thick, and the silicon pattern layer 106 may be about 1 μm thick.

Figure 1B:
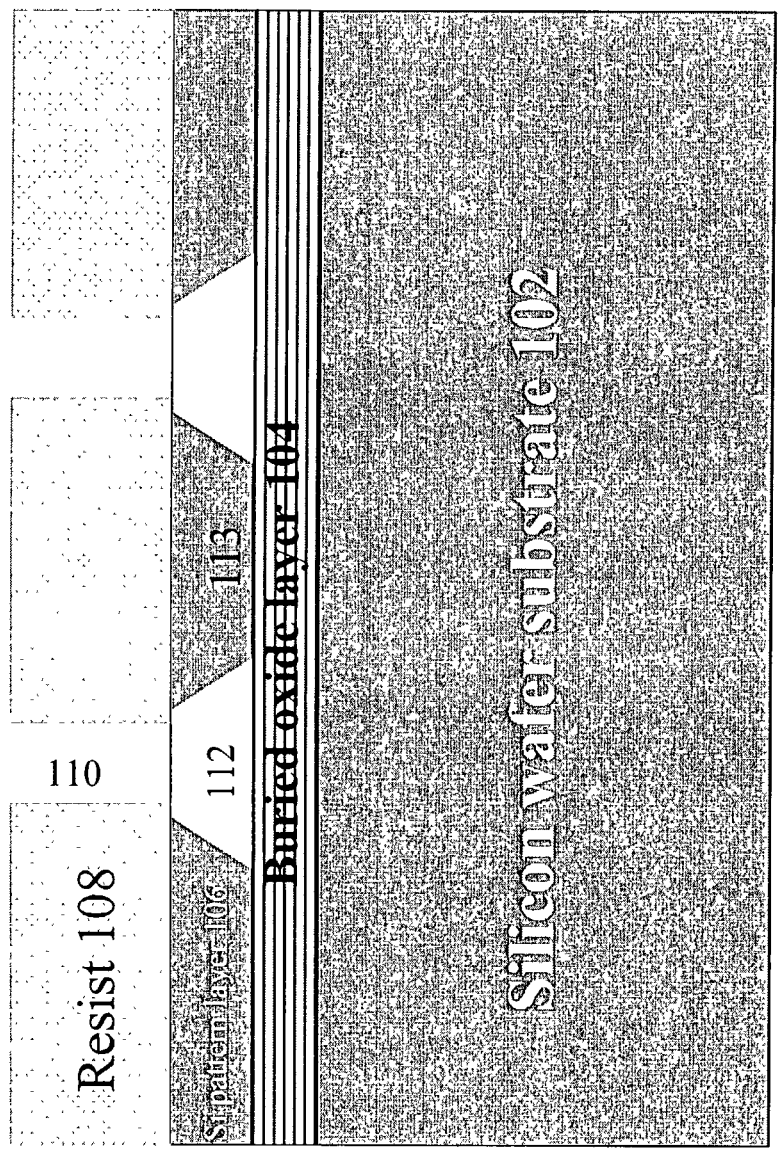

FIG. 1B is a cross section depicting the situation after the silicon pattern layer 106 has been etched. To go from FIG. 1A to FIG. 1B requires a few discrete steps. First, a layer of resist (e.g., photoresist) 108 may be deposited over the silicon pattern layer 106. The resist layer 108 may be, for example, about 1.0 μm thick. Second, the resist 108 may be lithographically patterned to expose a pattern of openings 110 in the resist 108. Third, the silicon pattern layer 106 may be etched through the openings 110 to expose a corresponding pattern of openings 112 and silicon 113 in the silicon pattern layer 106. These patterned areas (112 and 113) of the pattern layer 106 will form a suspended membrane at the end of the fabrication process. During the etching, care should be taken to avoid excessive undercutting of the remaining silicon of the pattern layer 106.

Figure 1C:
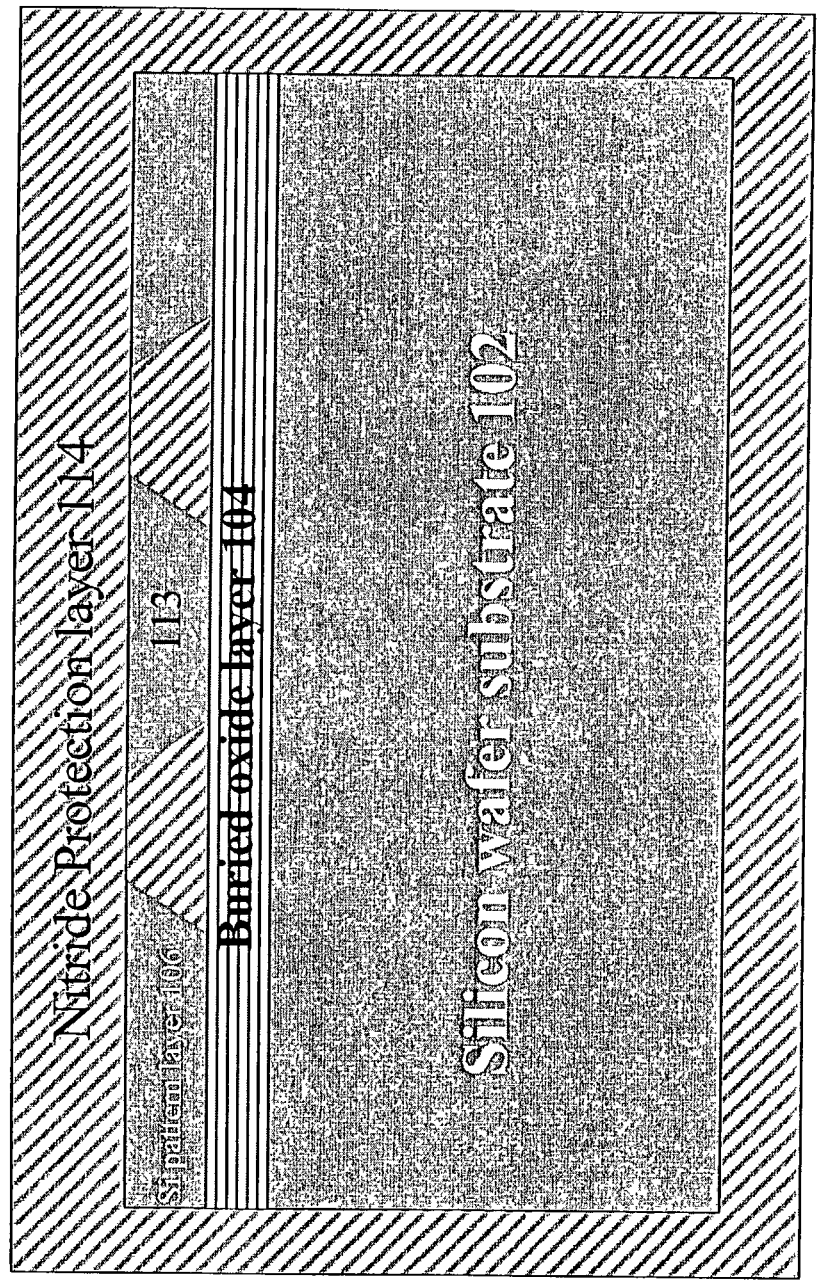

FIG. 1C is a cross section depicting the situation after deposition of a nitride protection layer (coating) 114. As seen from FIG. 1C, the nitride protection layer 114 surrounds all three layers of the wafer. As described below, this coating 114 will serve to protect a covered portion of the wafer during wet etching. The protective coating 114 may comprise, for example, a layer of LONH378 nitride that is about 1000 angstroms (0.1 μm) thick. LONH378 nitride refers to nitride formed using a specific low stress nitride recipe that is publicly available.

Figure 1D:
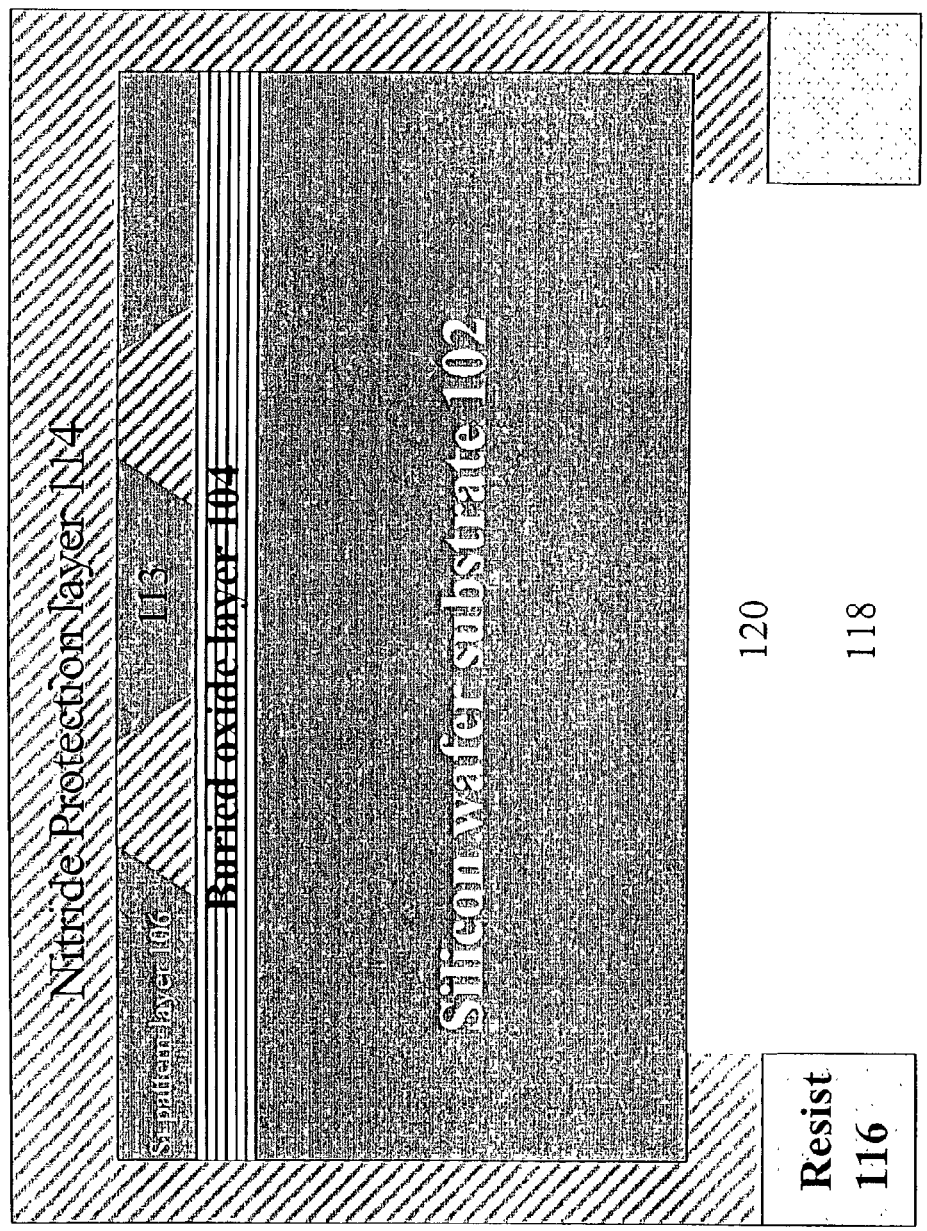

FIG. 1D is a cross section depicting the situation after etching of the nitride protection layer 114 on the substrate 102 side of the wafer. To go from FIG. 1C to FIG. 1D requires a few discrete steps. First, a layer of resist (e.g., photoresist) 116 may be deposited over the substrate 102 side of the wafer. The resist layer 116 may be, for example, about 1.6 µm thick. Second, the resist 116 may be lithographically patterned to expose openings 118 in the resist 116. Third, the nitride protection layer 114 may be etched through the openings 118 to expose corresponding openings 120 in the protection coating 114.

Figure 1E:
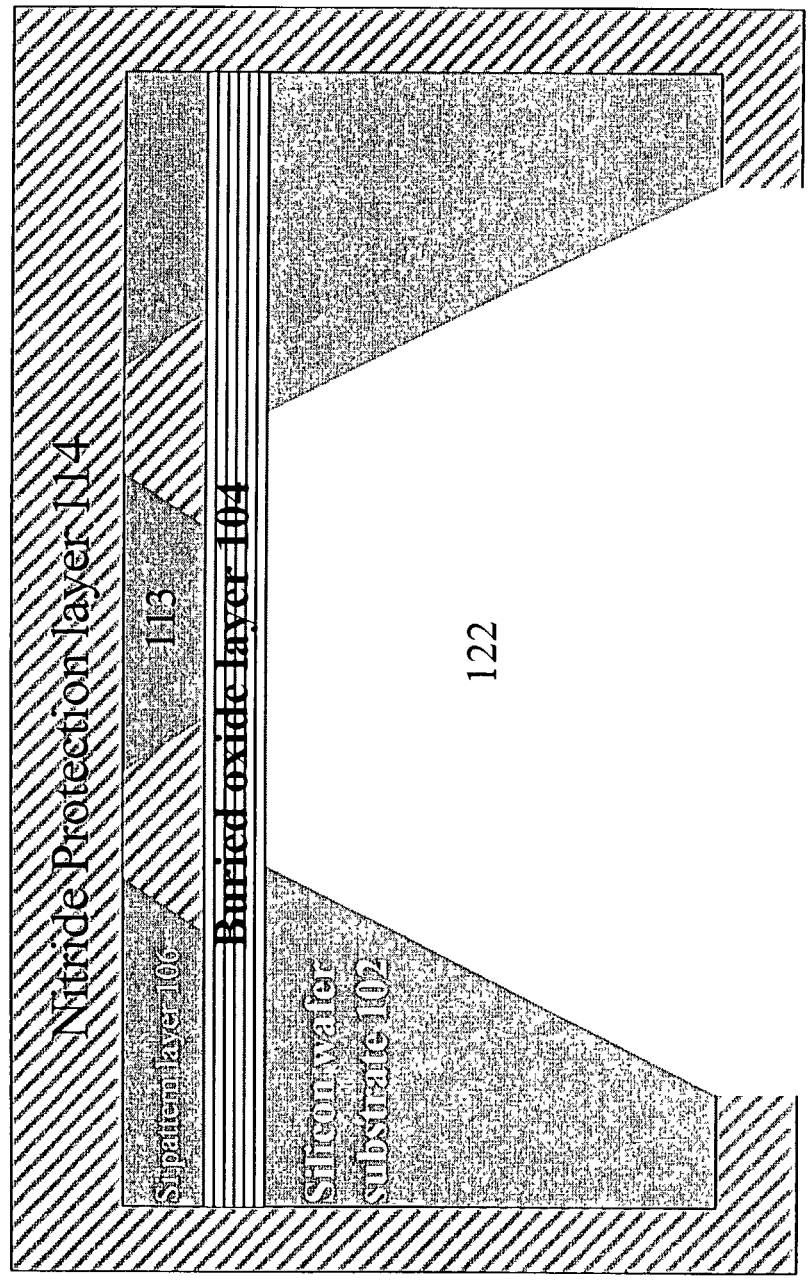

FIG. 1E is a cross section of the situation after the silicon substrate layer 102 has been etched. In this embodiment, the etching may be performed by a wet etch process. The wet etch may utilize, for example, a potassium hydroxide (KOH) solution to etch the exposed portions of the silicon substrate 102 while the other portions of the wafer are protected by the nitride layer 114. The etching exposes openings 122 through the substrate layer 102 and stops at the buried oxide layer 104. In this way, the buried oxide layer 104 separates the silicon pattern layer 106 from the silicon substrate 102 and protects the pattern layer 106 from the etching of the substrate 102. After the wet etch of the substrate 102, there should be a cleanup of the wet etch residues. Alternatively, in another embodiment, the etching may be performed by a combination of wet etching and dry etching steps. Advantageously, the dry etching may be used as the later etch step to achieve a more precise etching.

Figure 1F:
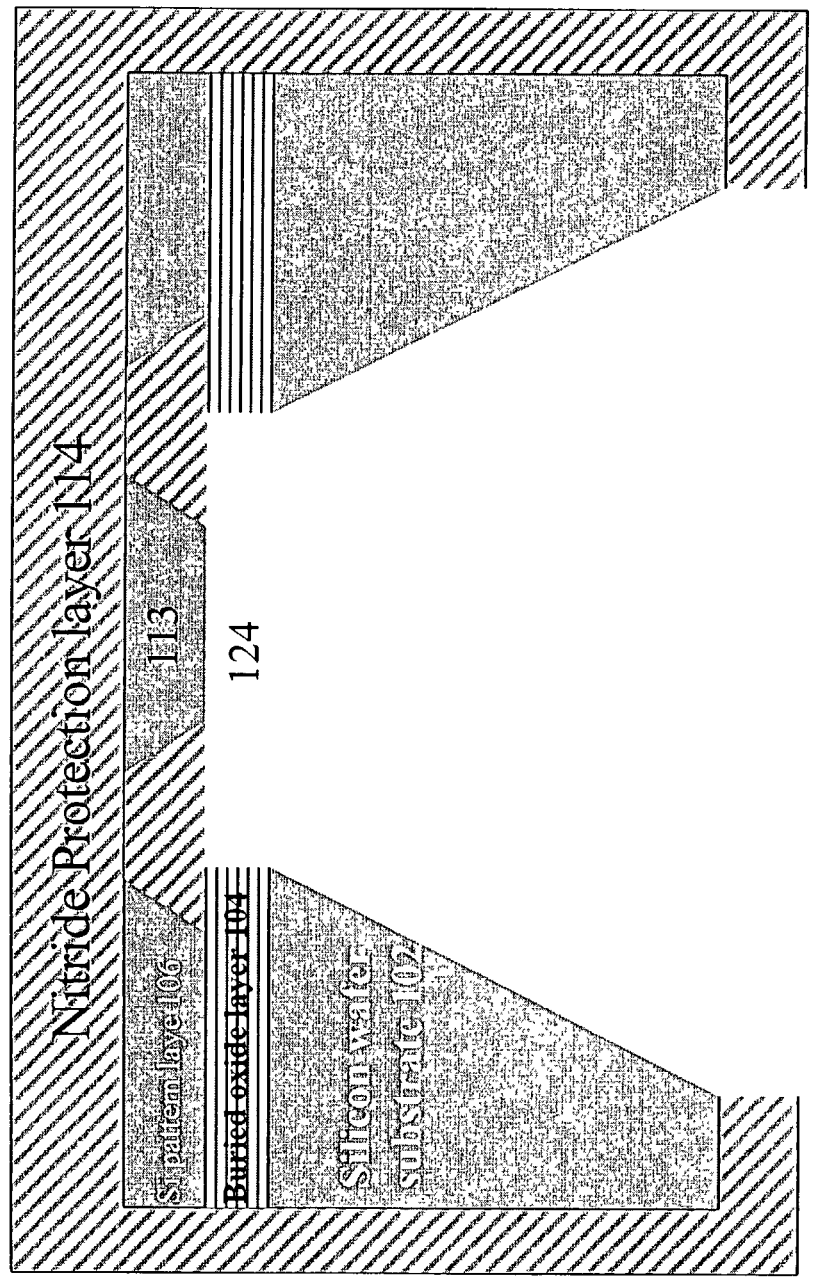

FIG. 1F is a cross section of the situation after the buried oxide layer 104 has been etched. The etching may be performed on the oxide layer 104 through the substrate openings 122. The etching creates corresponding openings 124 in the buried oxide layer 104. These openings 124 should be under the patterned areas (112 and 113) of the silicon pattern layer 106. The oxide etch may be performed, for example, by way of a hydrogen fluoride (HF) dip or by using HF vapor.

Figure 1G:
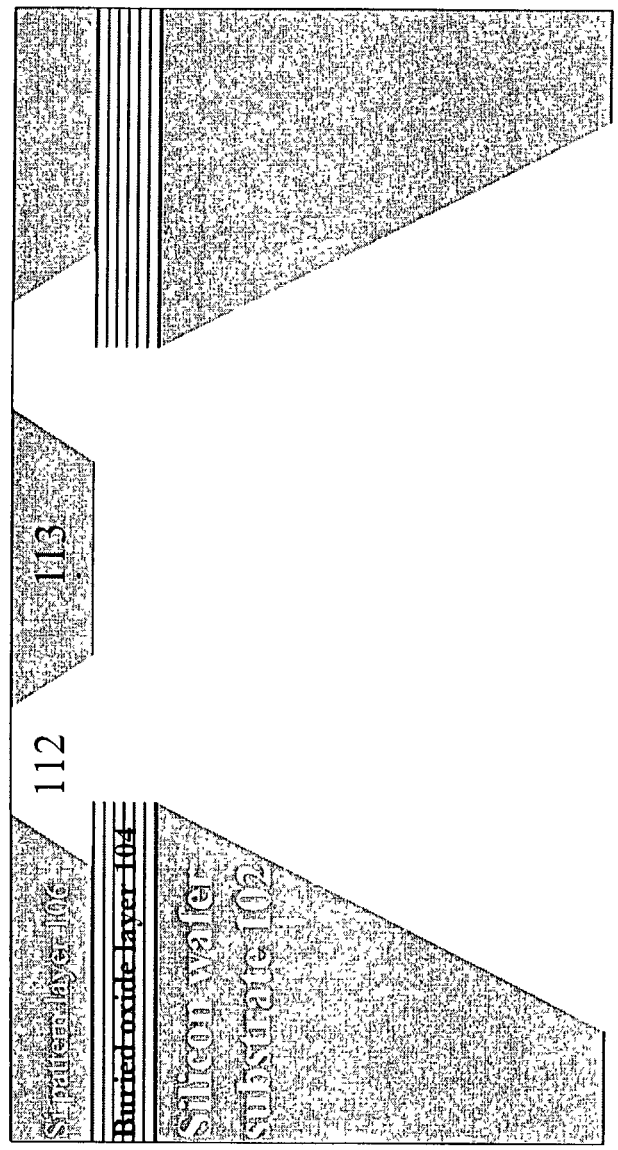

Finally, FIG. 1G is a cross section of the situation after the nitride protection layer 114 has been removed. The removal may be performed, for example, using a nitride wet bench for hot (for example, at 155 degrees Celsius) phosphoric acid etching (stripping) of the nitride 114. Hot phosphoric acid advantageously very selectively etches the nitride 114 while leaving the silicon (106 and 102) and oxide (104) materials substantially unaffected. This allows the nitride 114 to be fully removed.

As a result of this fabrication method, a suspended membrane calibration sample is formed. The calibration sample includes a suspended membrane comprising the patterned area (112 and 113) in the pattern layer 106. The pattern and thickness of the suspended membrane are such that the membrane is self-supporting. An example of such a pattern is described below in relation to FIGS. 6 and 7.

Figure 2:
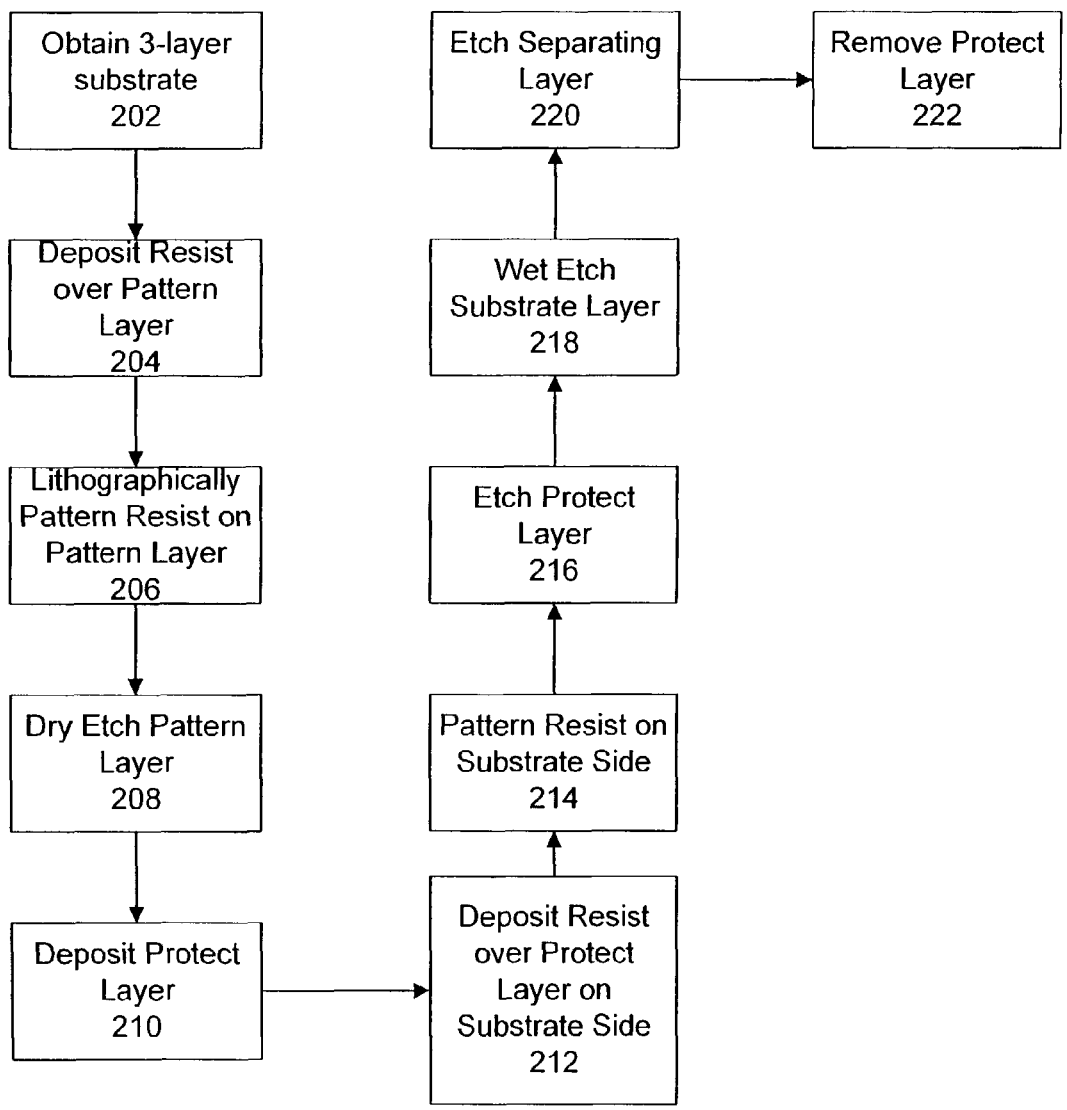
FIG. 2 is a flow chart depicting a first method for fabricating a calibration sample in accordance with one embodiment of the invention.

FIG. 2 is a flow chart depicting a first method 200 for fabricating a calibration sample in accordance with one embodiment of the invention. The method 200 as depicted includes eleven steps (202, 204, 206, 208, 210, 212, 214, 216, 218, 220, and 222). A specific example of this method 200 is described above in relation to FIGS. 1A through 1G.

In the first step 202, a three-layer substrate is obtained or created. The three-layer substrate should include a pattern layer, a separating layer, and a substrate layer. For example, the pattern layer may comprise a silicon pattern layer 102, the separating layer may comprise a buried oxide layer 104, and the substrate layer may comprise a silicon substrate 106. For other processes, the three layers may comprise different materials with similar functional characteristics. For instance, the separating layer may alternatively comprise a silicon nitride (SiNx) layer that may also serve as a stopper layer for both the front-side pattern etch and the back-side substrate etch.

In the second step 204, a resist material is deposited over the pattern layer. The third step 206 comprises lithographically patterning the resist to form openings in the resist. Subsequently, the fourth step 208 comprises etching the pattern layer through the openings in the resist to form patterned areas in the pattern layer. The etching may be performed by way of a dry (plasma) etch process. The patterned areas will form a suspended membrane at the end of the fabrication process.

In the fifth step 210, a protect layer or coating is deposited. The protect layer may comprise, for example, a nitride layer. The protect layer will serve to protect a covered portion of the wafer during wet etching.

In the sixth step 212, a resist material is deposited over the portion of the protect layer that is on the substrate layer side of the wafer. The seventh step 214 comprises patterning the resist to form openings in the resist. Subsequently, the eighth step 216 comprises etching the protect layer through the openings in the resist to form corresponding openings in the protect layer.

In the ninth step 218, the substrate layer is etched via the openings in the protect layer. For example, the etching may be done by way of a wet etch process. The etching exposes openings through the substrate layer and stops at the protect layer. In this way, the protect layer functions to separate the pattern layer from the substrate layer and protects the pattern layer from the etching of the substrate layer. Alternatively, in another embodiment, the etching may be performed by a combination of wet etching and dry etching steps.

In the tenth step 220, the separating layer is etched through the openings in the substrate layer. For example, if the separating layer comprises an oxide, the etch may be performed with an HF etch process. The etching creates corresponding openings in the protect layer. These openings should be under the patterned areas of the pattern layer.

Finally, in the eleventh step 222, the protect layer is removed. If the protect layer is a nitride, then the removal may be performed, for example, with a phosphoric acid etch process As a result of this fabrication method 200, a suspended membrane calibration sample is formed. The calibration sample includes a suspended membrane comprising the patterned area of the pattern layer. The pattern and thickness of the suspended membrane are such that the membrane is self-supporting.

Figure 3:
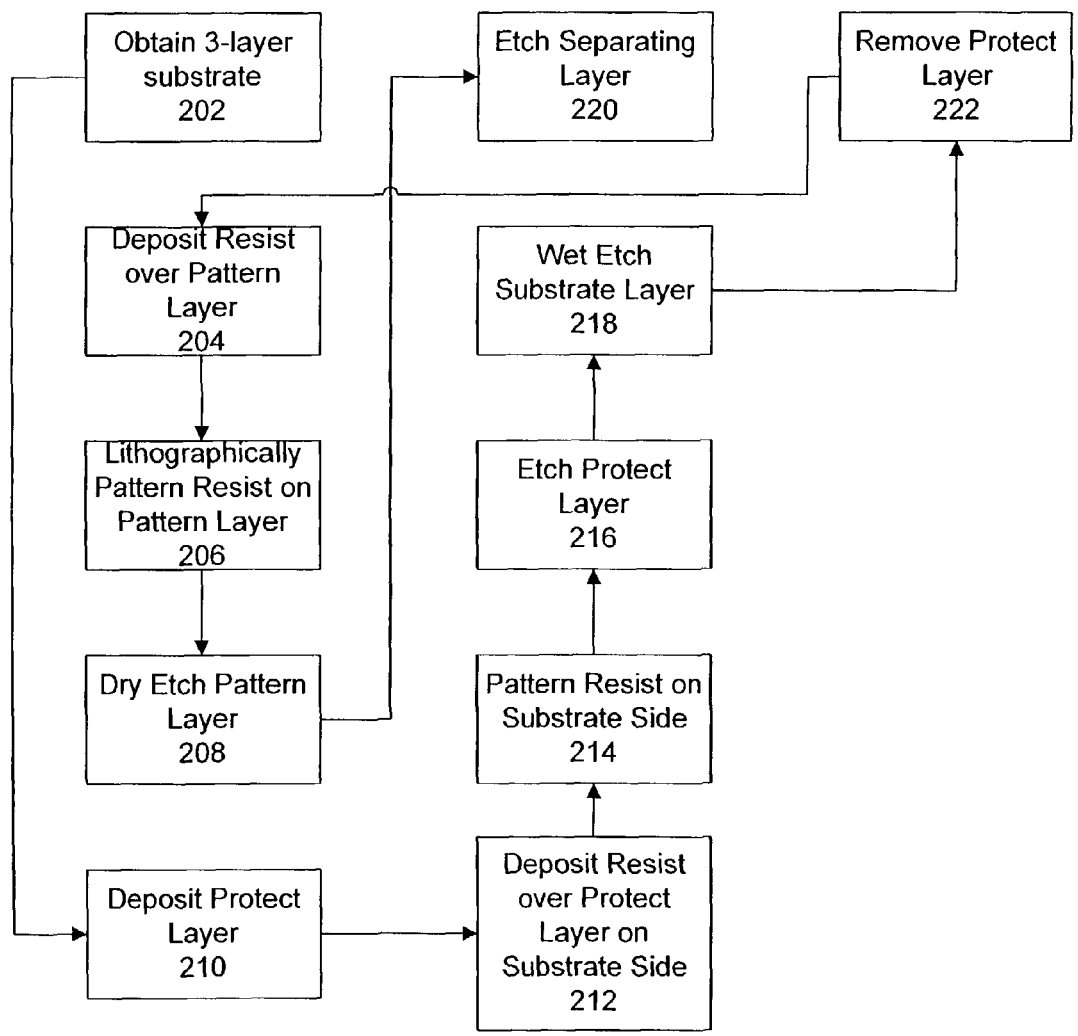
FIG. 3 is a flow chart depicting a second method for fabricating a calibration sample in accordance with another embodiment of the invention.

FIG. 3 is a flow chart depicting a second method 300 for fabricating a calibration sample in accordance with another embodiment of the invention. The second method 300 is similar to the first method 200 of FIG. 2. However, the order in which the steps are performed is different. In accordance with the second method 300, the substrate-side (back-side) deep etch is performed prior to the pattern-side (front-side) shallow etch. Specifically, the order in which the steps may be performed in accordance with the second method 300 is as follows: obtain 3-layer substrate 202; deposit protect layer 210; deposit resist over protect layer on substrate side 212; pattern resist on substrate side 214; etch protect layer 216; wet etch substrate layer 218; remove protect layer 222; deposit resist over pattern layer 204; lithographically pattern resist on pattern layer 206; dry etch pattern layer 208; and finally etch separating layer 220. This alternate order is illustrated in FIG. 3.

Figure 4:
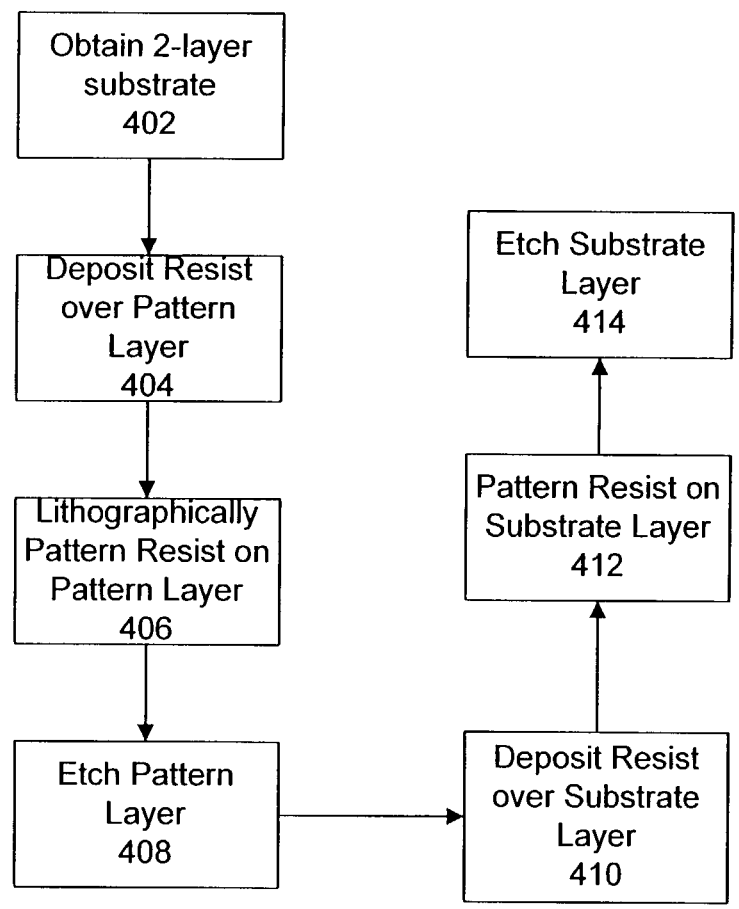
FIG. 4 is a flow chart depicting a third method for fabricating a calibration sample in accordance with another embodiment of the invention.
Figure 5:
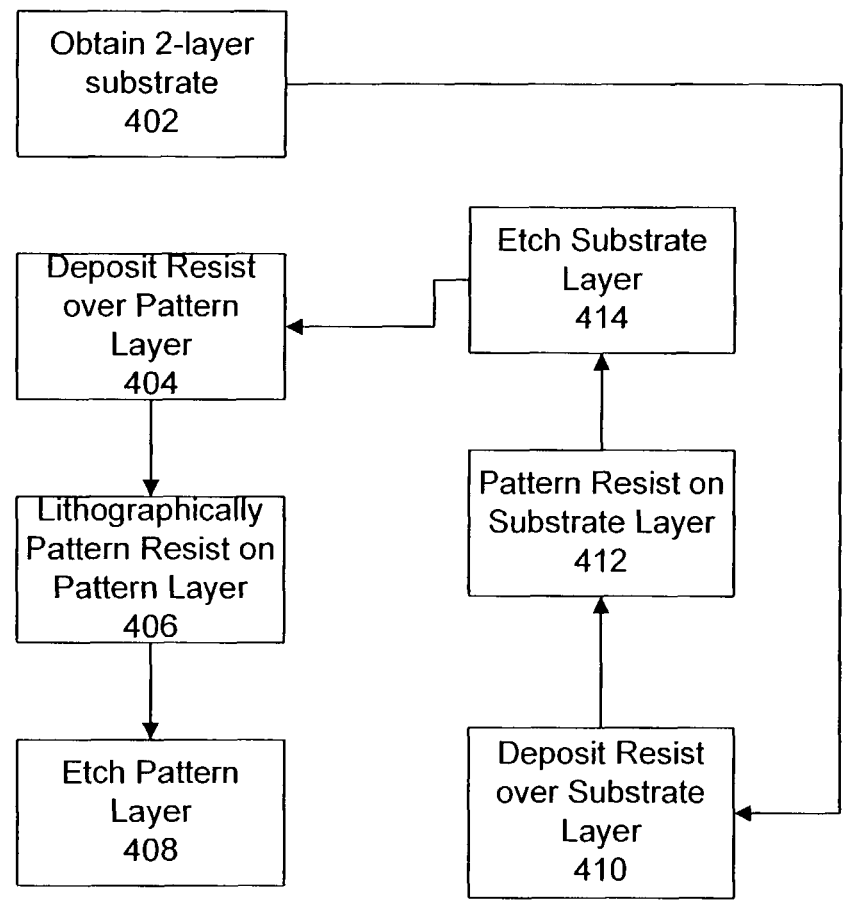
FIG. 5 is a flow chart depicting a fourth method for fabricating a calibration sample in accordance with another embodiment of the invention.

FIG. 4 is a flow chart depicting a third method 400 for fabricating a calibration sample in accordance with another embodiment of the invention. Similarly, FIG. 5 is a flow chart depicting a fourth method for fabricating a calibration sample in accordance with another embodiment of the invention. The third 400 and fourth 500 methods both begin with a first step 402 of obtaining or creating a 2-layer (instead of 3-layer) substrate. For example, the 2-layer substrate may comprise a silicon wafer substrate with a first layer that is p-doped and a second layer that is n-doped. One of the two layers comprises a pattern layer, and the other of the two layers comprises a substrate layer. Preferably, the pattern layer is the thinner of the two layers. In accordance with these methods 400 and 500, no separating layer is required because the etches that are performed are selective to one or the other of the two layers.

In accordance with the third method 400 of FIG. 4, the second step 404 comprises depositing resist over the pattern layer. The pattern layer comprises one of the two layers (for example, the p-doped layer on an n-doped substrate). The third step 406 comprises lithographically patterning the resist on the pattern layer, and the fourth step 408 comprises etching the pattern layer through the openings in the resist. The fifth step 410 comprises depositing resist over the substrate layer. The pattern layer comprises the other one of the two layers (for example, the n-doped substrate). The sixth step 412 comprises patterning the resist on the substrate layer, and finally the seventh step 414 comprises etching substrate layer through the openings in the resist.

The fourth method 500 depicted in FIG. 5 performs the steps in different order. In accordance with the fourth method 300, the substrate-side (back-side) deep etch is performed prior to the pattern-side (front-side) shallow etch. Specifically, the order in which the steps may be performed in accordance with the fourth method 500 is as follows: obtain or create 2-layer substrate 402; deposit resist over substrate layer 410; pattern resist on substrate layer 412; etch substrate layer 414; deposit resist over pattern layer 404; lithographically pattern resist on pattern layer 406; and finally etch pattern layer 408.

Note in the above description those of ordinary skill in the art will know other well-known steps that are implied to be in the methods of fabricating. For example, removal of the resist material after etching is implied.

Figure 6:
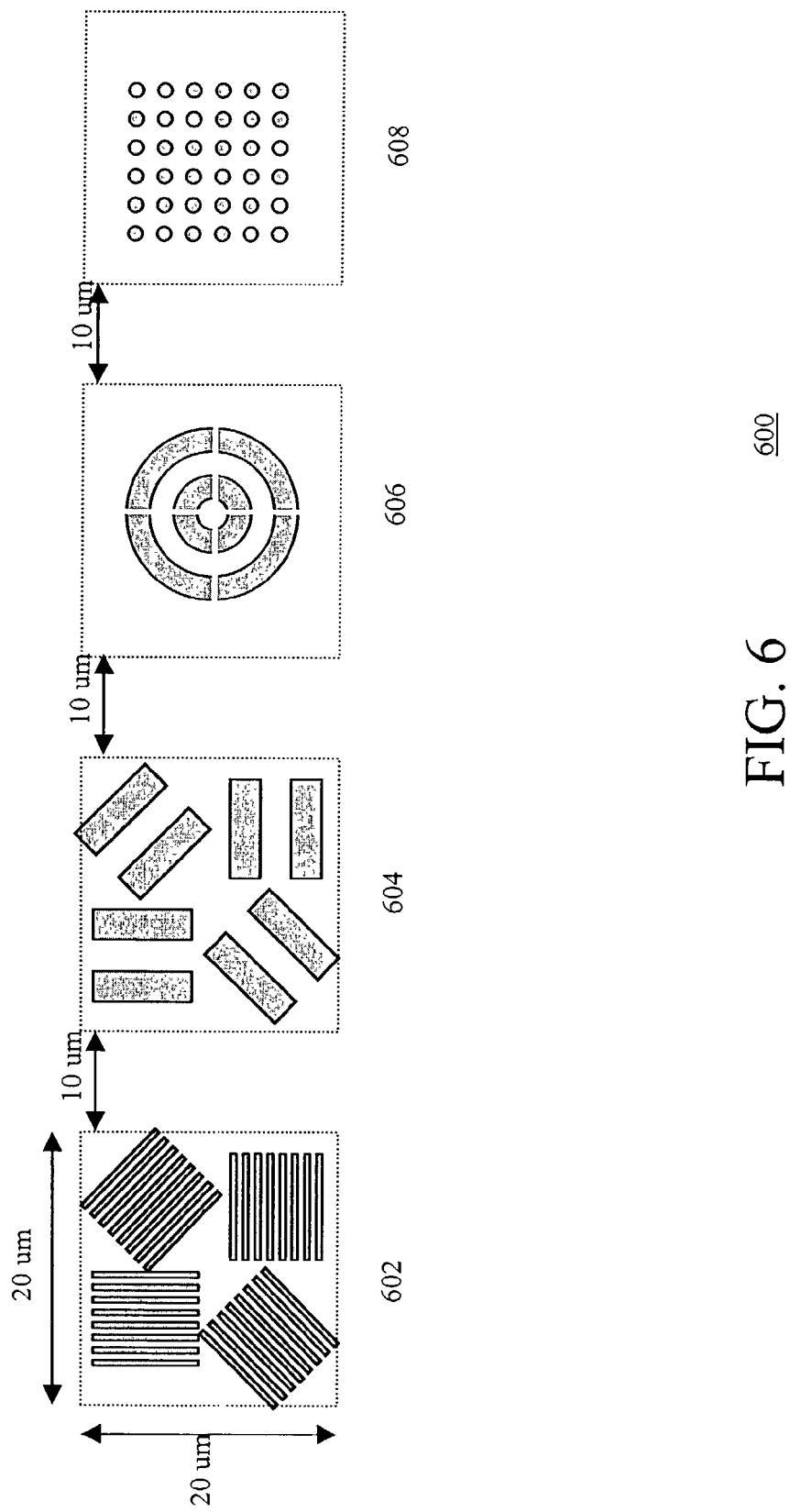
FIG. 6 is a top view depicting a set of calibration patterns that may be patterned into the calibration sample in accordance with an embodiment of the invention.

FIG. 6 is a top view depicting a set 600 of calibration patterns that may be patterned into the calibration sample in accordance with an embodiment of the invention. The darker regions in FIG. 6 are those regions of the pattern layer that are to be removed (etched away). The white regions are the regions to remain after etching and form the contrast and support for the patterns. The set 600 of calibration patterns includes four types of calibration patterns (602, 604, 606, and 608). The first calibration pattern 602 is a target for fine focusing calibration and (automatable) astigmatism correction. The second calibration pattern 604 is a target for coarse focus calibration. The third calibration pattern 606 is a target for deflection calibration. Finally, the fourth calibration pattern 608 is a target for manual astigmatism correction. Of course, the order of the targets in the set may be changeable. In one specific implementation, the targets may be about 20 μm by 20 μm in size and separated by about 10 μm. Of course, other dimensions are possible. The features in the targets may be less than a micron in size (i.e. submicron in size). In particular, features in the fine focus and astigmatism correction targets (602 and 608) may have submicron features.

Figure 7:
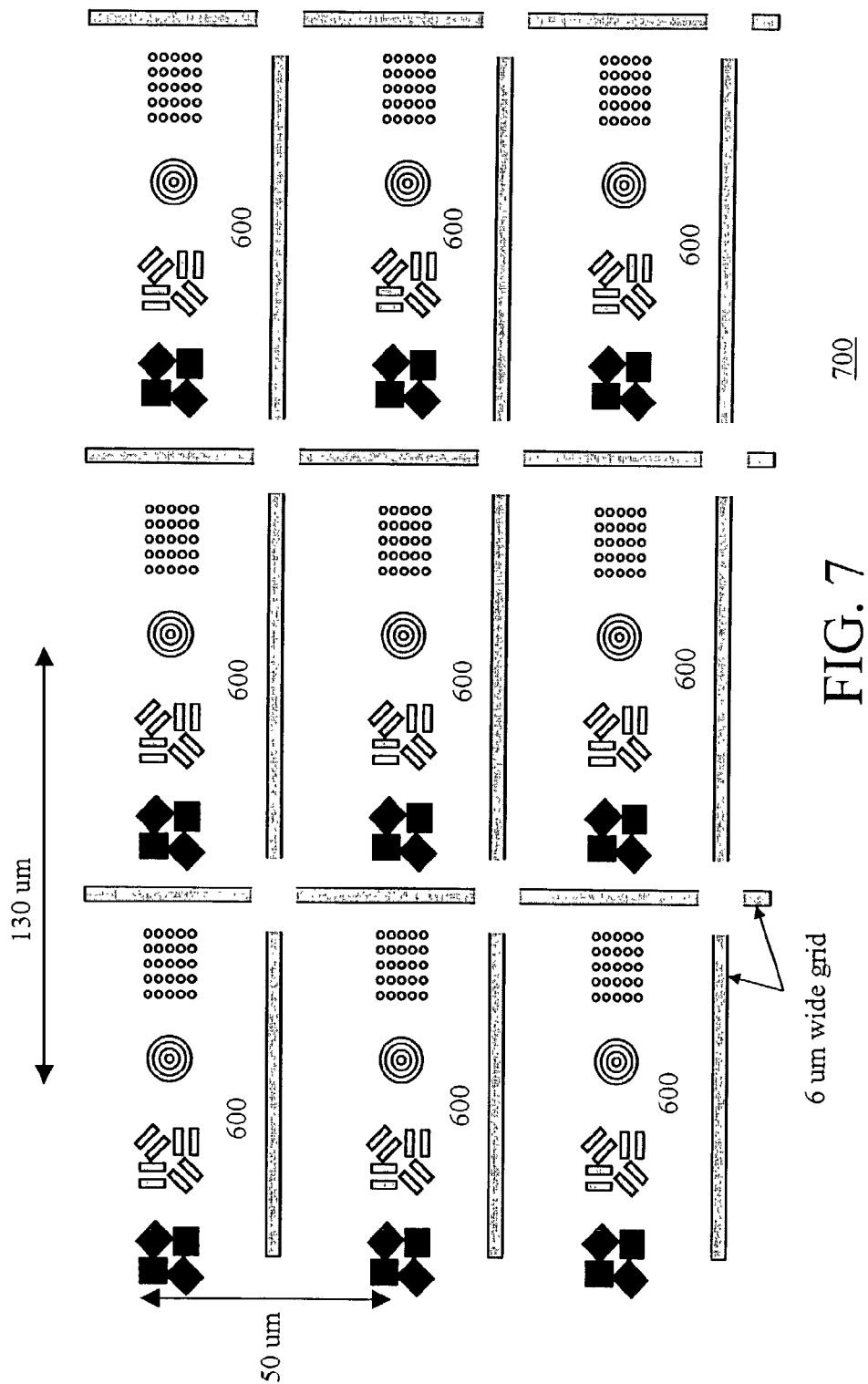
FIG. 7 is a top view depicting repetition of the set of calibration patterns in an array of cells in accordance with an embodiment of the invention.

FIG. 7 is a top view depicting repetition of the set 600 of calibration patterns in an array 700 of cells in accordance with an embodiment of the invention. As seen in FIG. 7, each cell in the array 700 may include a copy of the set 600 of calibration patterns. The cells may be demarcated by grid lines (for example, 6 μm wide). These grid lines are made to be discontinuous such that the array 700 may be self-supporting. In the specific implementation depicted, each cell of the array is 130 μm by 50 μm. Of course, other cell dimensions may be used.

Figure 8:
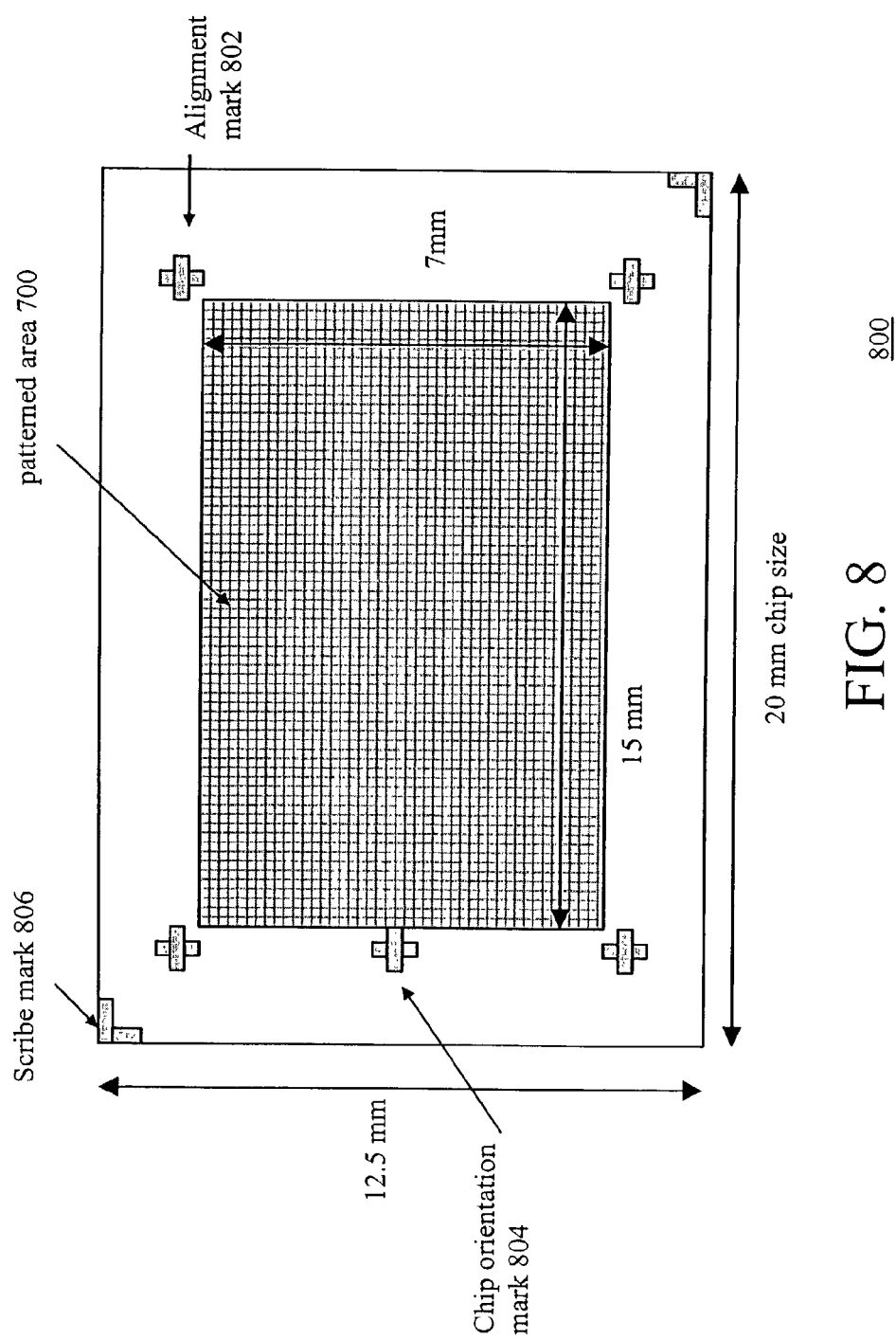
FIG. 8 is a top view depicting a layout of a calibration sample chip in accordance with an embodiment of the invention.

FIG. 8 is a top view depicting a layout of a calibration sample chip 800 in accordance with an embodiment of the invention. The calibration chip (die) 800 includes a patterned area that includes the array 700 of cells. In the specific implementation depicted, the chip size may be 20 mm by 12.5 mm, and the patterned area may be 15 mm by 7 mm. Of course, other dimensions may be used. The chip 800 may also include other useful marks, such as alignment marks 802, a chip orientation mark 804, and scribe marks 806.

Figure 9:
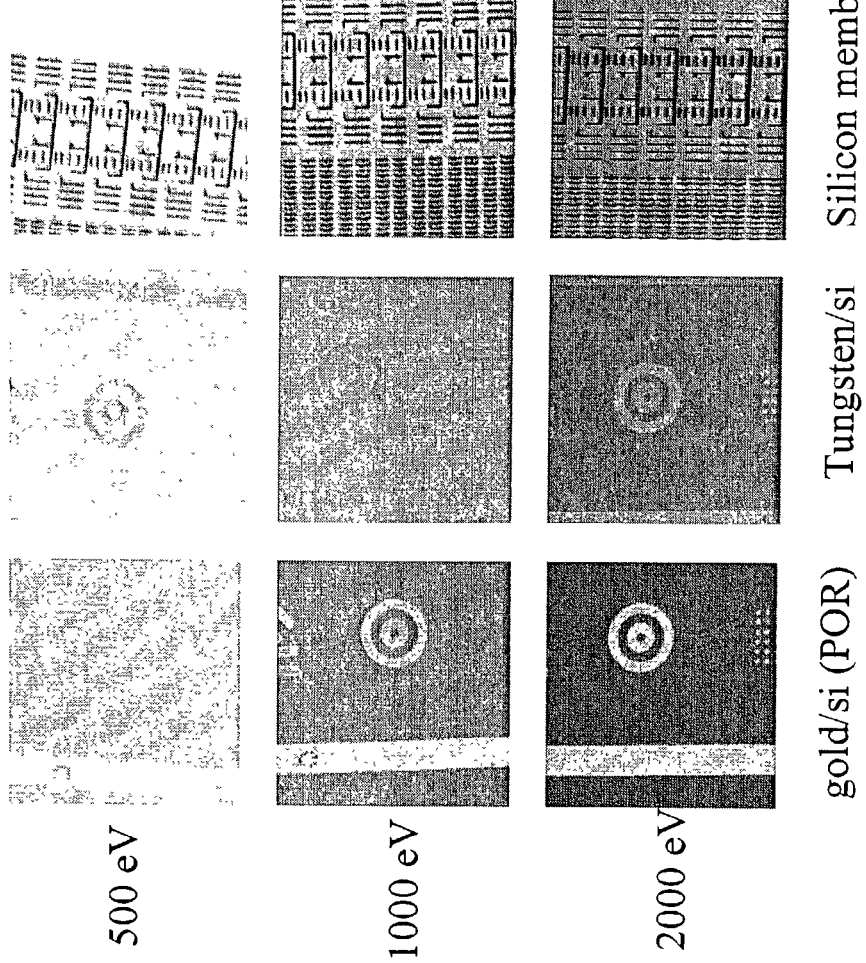
FIG. 9 illustrates results of a contrast study that shows the superior contrast characteristics of a silicon membrane at various electron beam landing energies.

FIG. 9 illustrates results of a contrast study that shows the superior contrast characteristics of a silicon membrane at various electron beam landing energies (in electron volts or eV). The nine images shown are in a grid with the row indicating landing energy (either 500 eV, 1000 eV, or 2000 eV) and column indicating type of sample.

The first column shows images from a gold calibration pattern on a silicon chip. As seen from the first column, the contrast is good at the higher landing energy (2000 eV) but becomes progressively poorer as the landing energy is decreased. At 1000 eV, the fine dots on the sample are no longer visible. At 500 eV, even the larger features on the sample become difficult to discern.

The second column shows images from a tungsten calibration pattern on a silicon chip. As seen from the second column, the contrast is okay at the higher landing energy (2000 eV) but is rather poor for the middle landing energy (1000 eV). At 500 eV, the contrast inverts (and is still pretty poor).

Finally, the third column shows images from a silicon membrane. While the silicon membrane in the third column is not a calibration pattern, it illustrates the advantages achievable by using the present invention. The images in the third column show contrast that remains high and with good resolution throughout the range of landing energies.

Note also that a suspended membrane calibration sample should have less contamination buildup (for example, from organic residue) than the conventional patterned silicon calibration chips. This is because such contaminations cannot build-up on the openings in the membrane. As a result, higher contrasts are maintained better with the suspended membrane calibration sample.

Figure 10:
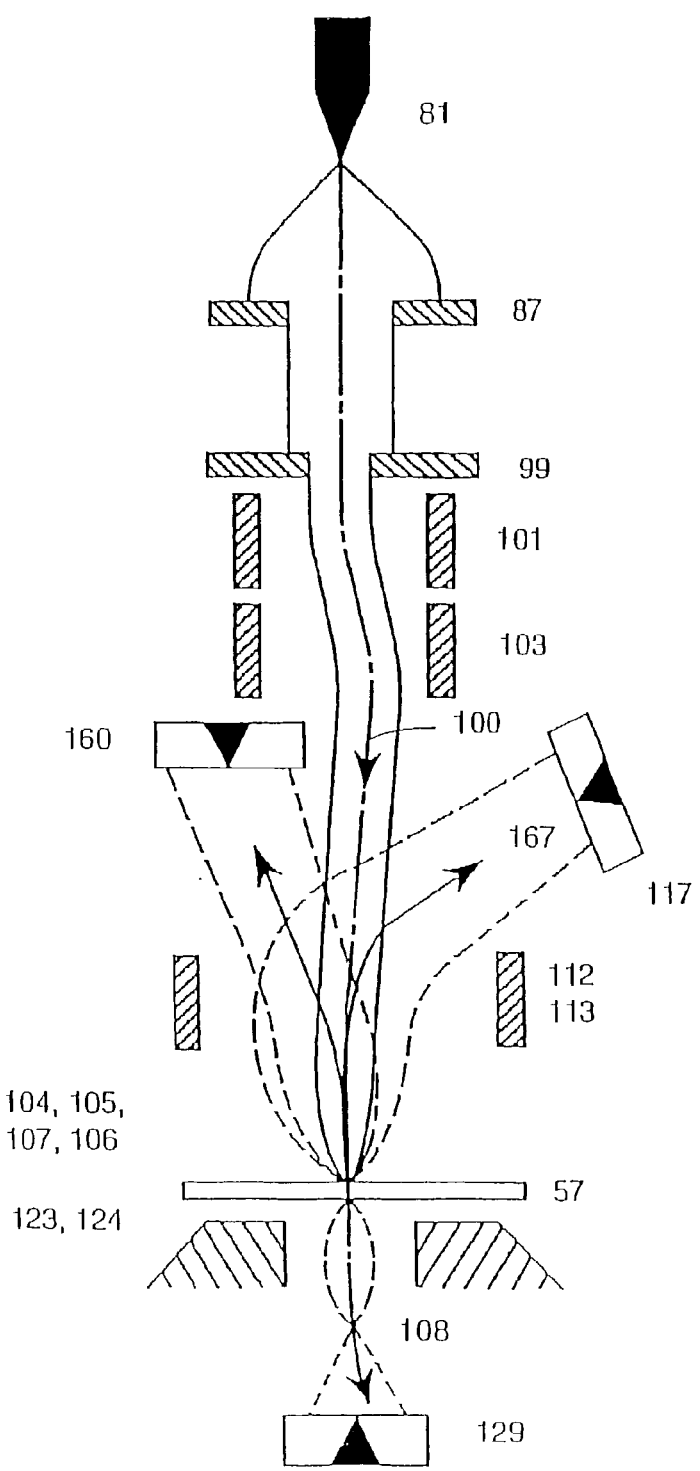
FIG. 10 is a diagram depicting an example of an electron beam system in accordance with an embodiment of the invention.

FIG. 10 is a diagram depicting an example of an electron beam system in accordance with an embodiment of the invention. The SEM system depicted in FIG. 10 is described in U.S. Pat. No. 5,578,821, entitled "Electron Beam Inspection System and Method," issued to Meisberger et al. and assigned to KLA-Tencor Corporation of San Jose, Calif. The disclosure of U.S. Pat. No. 5,578,821 (the Meisberger patent) is hereby incorporated by reference. Of course, the calibration sample of the invention may be also be used with other types of electron beam systems. For example, in addition to electron inspection systems, the present invention may be used in electron beam metrology systems or electron beam lithography systems.

Depicted in FIG. 10 is a simplified schematic representation of the paths of the primary, secondary, backscattered and transmitted electrons through the electron optical column and collection system for electron beam inspection. The various electron beam paths within the column and below substrate 57 are shown. Electrons are emitted radially from field emission cathode 81 and appear to originate from a very small bright point source. Under the combined action of the accelerating field and condenser lens magnetic field, the beam is collimated into a parallel beam. Gun anode aperture 87 masks off electrons emitted at unusable angles, while the remaining beam continues on to beam limiting aperture 99. An upper deflector (not depicted) is used for stigmation and alignment, ensuring that the final beam is round and that it passes through the center of the objective lens 104 comprising elements 105, 106 and 107. A condenser lens (not depicted) is mechanically centered to the axis defined by cathode 81 and beam limiting aperture 99. The deflection follows the path shown, so that the scanned, focused probe (beam at point of impact with the substrate) emerges from the objective lens 104.

In High Voltage mode operation, Wien filter deflectors 112 and 113 deflect the secondary electron beam 167 into detector 117. When partially transparent masks are imaged, the transmitted beam 108 passes through electrode system 123 and 124 that spreads the beam 108 before it hits the detector 129. In Low Voltage mode operation, the secondary electron beam is directed by stronger Wien filter deflections toward the low voltage secondary electron detector 160 that may be the same detector used for backscatter imaging at high voltage. Further detail on the system and its operation is described in the Meisberger patent.

In accordance with an embodiment of the invention, the suspended membrane calibration sample may be incorporated into an electron beam system, such as the electron inspection system depicted in FIG. 10. The suspended membrane calibration sample may be mounted within such a system. In a calibration mode, the primary beam may be deflected onto the calibration sample. In a preferred embodiment, the electron beam system does not re-use calibration patterns. Instead, the system uses an un-used calibration pattern from the calibration sample for each calibration process. This may be done by serially going to a next calibration pattern for each time a calibration is run. Advantageously, the higher contrasts obtainable using a suspended membrane calibration sample should provide for the calibration to be performed in shorter time periods.

In alternative embodiments of the invention, the suspended membrane calibration sample may be incorporated and used into other types of electron beam systems. The suspended membrane calibration sample may also be incorporated and used in ion beam systems.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. An electron beam inspection or metrology apparatus, the apparatus comprising:
   an electron source;
   an electron beam generated from the source;
   a focusing column and lens assembly configured to focus the charged-particle beam onto a substrate in an imaging mode;
   a secondary electron detector configured to detect secondary electrons from a surface of the substrate;
   a calibration sample within the apparatus; and
   a suspended membrane of the calibration sample which is structurally supported solely at an outer perimeter of the calibration sample without structural supports internal to the outer perimeter,
   wherein the suspended membrane includes a plurality of substantially identical cells in an array so as to provide a multitude of substantially identical calibration targets, each substantially identical cell comprising submicron features for fine focus and astigmatism correction that contrast the membrane against empty space.

2. The electron beam apparatus of claim 1, wherein the suspended membrane comprises a silicon layer.

3. The electron beam apparatus of claim 1, wherein each cell further includes a target for coarse focus.

4. The electron beam apparatus of claim 1, wherein each cell further includes a deflection target.

5. The electron beam apparatus of claim 1, wherein each cell further includes a manual astigmatism target.

6. The electron beam apparatus of claim 1, wherein the apparatus is configured to focus the electron beam at a single cell at a time during said calibration mode and is further configured so as to not re-use a cell and instead uses an un-used cell from the calibration sample for each calibration process under the calibration mode.

7. The electron beam apparatus of claim 1, wherein lithographic patterning and etching is used during fabrication of the suspended membrane of the calibration sample.

8. The electron beam apparatus of claim 1, wherein the apparatus comprises an electron beam inspection system.

9. The electron beam apparatus of claim 1, wherein the apparatus comprises an electron beam metrology system.

10. A suspended membrane calibration sample for an electron beam inspection or metrology apparatus, the calibration sample comprising:
    a plurality of calibration patterns in an array of substantially identical cells so as to provide a multitude of substantially identical calibration targets; and
    a suspended membrane which is internally self-supporting in that the membrane is structurally supported only at an outer perimeter of the calibration sample and which includes the plurality of calibration patterns,
    wherein the calibration patterns include submicron features for fine focusing correction and for astigmatism correction, and
    wherein the submicron features contrast the membrane against empty space.

11. The calibration sample of claim 10, wherein suspended membrane comprises a silicon layer.

12. The calibration sample of claim 10, wherein the calibration patterns further include a target for coarse focus.

13. The calibration sample of claim 10, wherein the calibration patterns further include a deflection target.

14. The calibration sample of claim 10, wherein the calibration patterns further include a manual astigmatism target.

15. The apparatus of claim 1, wherein the apparatus includes a separate calibration mode in which the beam is deflected onto the calibration sample and not onto the substrate being imaged.

* * * * *